United States Patent [19]

Jacob et al.

[11] Patent Number: 5,733,551
[45] Date of Patent: Mar. 31, 1998

[54] PROCESS FOR PREPARING SPHEROIDS OF PLANT ORIGIN

[75] Inventors: Maurice Jacob, Montpellier; Bernard Bataille, St. Gely du Fesc; Olivier Jacob, Montpellier; Michel Iderne, Strasbourg, all of France

[73] Assignee: Apis Spheromont, Strasbourg, France

[21] Appl. No.: 495,964

[22] Filed: Jun. 28, 1995

[30] Foreign Application Priority Data

Jun. 28, 1994 [FR] France ................................. 94 08358

[51] Int. Cl.⁶ ............................................. A61K 35/78
[52] U.S. Cl. ...................... 424/195.1; 424/494; 424/499
[58] Field of Search ................................. 424/484, 485, 424/486, 488, 499, 500, 195.1, 520, 600, 494; 514/948, 951

[56] References Cited

PUBLICATIONS

Remington's Pharmaceutical Sciences, Mac Publishing Co., 18th Ed. "Spheronization", p. 164, 1990.

*Primary Examiner*—Jean C. Witz
*Attorney, Agent, or Firm*—Davis and Bujold

[57] ABSTRACT

Compositions of natural, especially plant, constituents in the form of spheroids in particular of the medicinal type and formulations necessary to their preparation by a technical extrusion and spheronization system. Compositions characterized by the direct use of large quantities of solutions of natural, especially plant, origin such as liquid extracts adsorbed by natural or synthetic polymer-type substances. These various components are selected so that their combination permits the obtainment of a mass of a plasticity compatible with the technical extrusion and spheronization system. According to the process, liquid extract is prepared, this extract is incorporated in a substance of a polymeric type, the correctly moistened mass is extruded by microextrusion techniques and the extrudates are spheronized and then dried and calibrated.

17 Claims, No Drawings

5,733,551

PROCESS FOR PREPARING SPHEROIDS OF PLANT ORIGIN

FIELD OF THE INVENTION

The invention relates to compositions of substances of natural origin, such as plants, trace elements, minerals, vitamins or animal constituents in the form of spheroids and more especially the formulation of galenic forms corresponding to medicinal, dietetic or alimentary spheroids prepared with solutions especially of plant origin.

The invention also relates to the method of preparing these spheroids from a process of micro-extrusion and spheronisation.

It also relates to the applications resulting therefrom for the oral administration to humans and animals of spheroids which may contain up to 30 % natural water-alcohol soluble components.

TECHNICAL BACKGROUND TO THE INVENTION

It is known to prepare extracts of plant products in the form of extractive plant solutions obtained by maceration, infusion, decoction, digestion or lixiviation.

Use of these liquid extracts exhibits some disadvantages, in particular in relation to their physical and chemical instability during preservation, the characteristic low plant constituent content or frequent presence of ethyl alcohol in greater or lesser quantities, which is not generally desired for the oral administration of products, particularly when they are medicinal products.

At present, to transform such extracts into dry extracts capable of limiting the above-mentioned disadvantages, processes are used which make use of a considerable input of heat, such as nebulisation, drying on rollers or evaporation under reduced pressure.

If these processes permit the obtainment of dry plant components in the form of powders which are easier to use, in particular which may be orally administered, on the other hand they require an increase in temperature which may alter the characteristic constituents of the plant concerned. Moreover, these dry extracts are very often hygroscopic, which leads, through the resorption of moisture, to lump formation, the risk of modification of the physical and chemical stability and problems of reproducibility and of handling.

In FR 2 683 874 the preparation of an extract of active principles in dry, adsorbable form, in particular of plant origin, is effected. This preparation consists, on the one hand, in preparing an extract in liquid medium by a conventional process, then depositing this extract on grains of an adsorbent substrate, and on the other hand in causing these previously calibrated grains to be adsorbed into and onto porous microgranules of nebulised excipient.

In such a case, use involves the mixing of grains enriched with, especially plant, active principles with pre-formed porous grains to prepare and stabilise the extracts of active principles.

As far, moreover, as extrusion and spheronisation are concerned, these constitute a relatively complex technical system used in particular for the preparation of pharmaceutical products in the form of small spheres or spheroids (from 300 to 1,500 microns average diameter). The manufacturing process consists in granulating, that is to say moistening a pulverulent mass with the aid of an aqueous or non-aqueous liquid, then extruding this moist mass through a die with calibrated orifices, then rendering spherical, that is to say spheronising, the extruded product.

During the extrusion process the moistened mass is compressed and transformed by drawing into compact filaments of generally circular calibrated section known conventionally as extrudates. To obtain spheroids, these extrudates are placed in a cylindrical apparatus enclosing in its lower part a disk rotating at variable, controlled speeds, known as a spheroniser. Under the effect of the centrifugal force exerted by the controlled rotation of the rotating disk, the extrudates break up regularly and are then turned into spheres by a rolling/binding effect.

It must be admitted that, to be capable of subjection to this process, the moistened mass must exhibit a degree of specific, controlled plasticity in order to enable production of the extrusion and spheronisation processes, that is to say the deformation over a first period of the moistened mass and the transformation thereof over a second period into extrudate, then into spheroids. Obtainment of a suitably moistened mass to correspond to the specific plasticity necessary to the good functioning of the extruder and the production of extrudates capable of transformation into spheroids requires the selection of generally powdery substances with the ability to adsorb and absorb predetermined quantities of aqueous or non-aqueous moistening liquids. The satisfactory relationship between the quantity of moistening liquid and the quantity of powder has to be determined to obtain the plastic mass conformed to the operations of extrusion and then spheronisation.

Similarly, it has been noted that the possibility of transforming the extrudates into spheroids of homogenous sphericity and predefined regular granulometry also depends on the plastic characteristics of the extrudates and thus of the characteristics linked to the spheronisation operation proper, that is to say to the speed and duration of the rotation of the revolving disk.

AIMS OF THE INVENTION

The aim of the invention is to establish simplified formulations which permit the administration to people or animals of liquid preparations containing natural substances in dry form. It further aims to provide a process using extrusion and spheronisation, which permits the preparation of spheroids with defined technical characteristics, using the simplified formulations while ensuring physical and chemical temporal stability of the, especially plant, components used without thermal degradation.

In other words, the invention also aims to provide a formulation/process system for preparing spheroids based on solutions of natural origin which are easy to use, enabling the obtainment of, for example, dry plant constituents which may be absorbed orally in the form of temporally stable spheroids and are easier to control and reproduce.

These spheroids are presented as they are or coated, loose, in a dosing distributer or as hard gelatine capsules, tablets, in sachets or any other form designed for this type of administration.

One of the aims of the invention is to use the intrinsic adsorbent and absorbent properties increased with respect to aqueous and non-aqueous liquids such as water or mixtures in any proportions of water and ethyl alcohol in particular, of substances used alone or together, of natural or synthetic polymer type. These substances may correspond to base materials used in pharmacy, in dietetics or nutrition, such as microcrystalline celluloses, microfine celluloses, starches, modified starches, various polysaccharides and, in general, base materials exhibiting an adsorbent and absorbent power with respect to aqueous and non-aqueous liquids conferring to the moistened mass the plastic qualities necessary to the production of extrudates and spheroids by the process of extrusion and spheronisation.

One of the characteristics of the invention is the ability to combine with the adsorbent and absorbent substances different substances such as simple low energy sugars, mineral and organic substances which may correspond in particular with lactose, sorbitol, D-mannitol, maltodextrins, carbonates, citrates. These substances constitute auxiliary substances.

One particularly desirable combination may contain a microcrystalline cellulose constituting from 20% to 80% of the total mass to be moistened, lactose constituting 80% to 20%, gelatin of variable jellifying power or polyvinyl pyrrolidone or a cellulose derivative (ethyl, methyl, carboxy) constituting less than 10%. Use within the scope of the invention of these auxiliary substances depends on the end use of the prepared spheroids, in other words, depending on whether the natural and plant constituents supported by the spheroids are capable of rapid release (less than thirty minutes) or gradual release (generally over a period of over an hour) in a natural or artificial solution.

Another characteristic of the invention is the use of auxiliary substances to give the texture of the spheroids a porosity of variable volume which may reach 100 mm3 per gram of spheroids, adapted to the rapid or gradual release of the natural, for example plant, constituents in a natural or artificial solution. The desirable combination in the preceding paragraph fulfils a rate of defined porosity.

Another characteristic of the invention is to use as moistening liquids solutions of natural, for example plant, origin, which correspond to aqueous or non-aqueous solutions containing natural characteristic constituents. It is usual, in particular, for the liquid to be a mixture of variable proportions of water and ethyl alcohol, proportions related to the solubility characteristics of the natural constituents.

In this way, to obtain a mass of plasticity compatible with the technique of extrusion and then spheronisation, the mass of adsorbent and absorbent substance has to be moistened by a quantity of liquid between 50 and 250% of the mass to be moistened. It has been noted that, apart from these limit values, the moistened mass does not exhibit the characteristics of plasticity required for good operation of the extruder, whether the mass is too liquid and does not permit the obtainment of extrudates or whether the mass is too dry, leading to overheating of the mass as well as of part of the apparatus during extrusion, which leads to a blockage in operation of the apparatus.

Another characteristic of the invention is that the plasticity required for extrusion and then spheronisation is dependent on the relationship existing between the quantity of moistening liquid and the quantity of mass to be moistened. In this way, the invention defines, in particular for the use of microcrystalline celluloses, that the quantity of moistening liquid represented by a solution of plant origin is between 90% and 150% of the quantity of microcrystalline celluloses used.

According to another characteristic of the invention, the strong adsorbent and absorbent power of the polymeric-type substances serves to retain and fix in and on the physical structures of said substances the constituents of the solution of natural origin conventionally known as liquid extract, plant tincture, extractive solution, solution of dry extract, mother tincture, tincture of fresh herbs, spirit, solution of plant constituent and more broadly plant solutions.

Owing to their increased power of adsorption and absorption of the solutions of natural origin, these polymeric-type substances may thus serve to support various compositions usable orally in particular for humans or animals for therapeutic, dietetic, preventive or nutritional purposes.

Another important aim of the invention is to present these compositions in the form of spheroids prepared by an improved process of extrusion and spheronisation. This system is adapted in its technical characteristics to exploit the simplified formulations enabling the preparation of spheroids of homogeneous sphericity and of pre-defined regular granulometry and containing in large concentrations constituents characteristic of natural products. Adaptation of the technical characteristics leads, on the one hand, to the definition of the extrusion die and speed and temperature control during extrusion, which temperature does not exceed thirty degrees Celsius, and, on the other hand, to the definition of the speed and duration of spheronisation, to exploit the simplified formulations enabling preparation of the spheroids according to the above-defined specifications.

One particular characteristic of the invention comprises preparing the extrudates and then the spheroids of plant solution from a liquid extract as defined by the Pharmacopoeia, using a mass of microcrystalline cellulose substantially equal to the mass of liquid extract. Determination of this ratio permits the preparation of spheroids of a granulometry of between 350 microns and 1,000 microns, for a yield of at least 95% of the mass of spheroids produced. In this case, it is usual to use an extrusion die comprising orifices of 800 microns in opening diameter and 800 microns in length which is also the thickness of the die. It is essential for the characteristics of the spheroids that the relationship between the diameter of the orifices and their length to be substantially equal to one. In this case, the extrusion speed is 100 revolutions per minute for an extrusion apparatus of the GABLER twin-screw type or of any other type. The spheronisation cycle for a spheroniser apparatus 60 cm in diameter or otherwise lasts for ten minutes. It should be emphasized that the spheronisation period is split into two essential phases, one with a faster rotational speed, 740 rev/min for example, for 90% of the time and a terminal phase with a lower rotational speed, 500 rev/min for example, for a complementary period. In this case, the spheroids resulting from spheronisation are dried at a temperature not exceeding forty degrees Celsius.

Furthermore, the invention also permits the preparation of spheroids which may contain large concentrations of characteristic plant constituents. According to one characteristic of the invention, it is the use of substances of increased adsorbent and absorbent power with respect to aqueous and non-aqueous liquid (a minimum of 100% of liquid adsorbed and absorbed), in particular of plant solutions of the liquid extract type, which ensures an increased content of characteristic plant constituents on and in the prepared spheroids. Thus, a hard gelatin capsule of standard size no. 1 may contain from 400 to 450 mg of spheroids supporting constituents of from 400 to 450 mg of liquid extract.

It is especially possible to prepare spheroids containing at least the same quantity of characteristic plant constituents as contained in the same mass of dry plant.

The invention also permits the production of spheroids free of energy-giving sugars such as saccharose in particular and relieved of all liquids and in particular ethyl alcohol when the plant or other solutions used contain them, and supporting all the plant constituents contained in the "plant solutions" used in the spheroid preparation. This characteristic is obtained without great increase in the temperature, which does not exceed 40° C., avoiding significant alteration of the characteristic plant constituents.

SUMMARY OF THE INVENTION

This process for the preparation of spheroids based on solutions of products of natural and plant origin, especially adsorbable orally, is characterized in that it comprises:

- firstly, preparing in known manner a solution of products of natural and in particular plant origin, from one or more plants or parts of fresh or dried plant(s) in a liquid medium specific to the characteristic constituents of said plants;
- secondly, moistening with the plant solution a substance of polymer type or a mixture of a plurality of these substances;
- then, extruding this correctly moistened mass, having previously defined the extrusion die and the extrusion speed, while controlling the extrusion temperature, which does not exceed 30° C.;
- then, spheronising the extrudates previously obtained, defining a programme of rotational speeds for the revolving disk;
- finally, drying the spheroids obtained under conventional technical conditions, without exceeding a temperature of forty degrees Celsius.

DETAILED DESCRIPTION OF THE INVENTION WITH THE AID OF EXAMPLES

The following Examples enable a better explanation of the invention.

Example 1

A form of spheroid prepared in the above-described manner contained 17.2% of HARPAGOPHYTON water-alcohol-soluble constituents corresponding to 100.0 parts of dried plant and being of the following composition.

For a batch of approximately 5,000 g of spheroids the formula comprises:

| Ingredient | Quantity in % by weight |
| --- | --- |
| HARPAGOPHYTON liquid extract | 4,275.0 g |
| Microcrystalline cellulose | 4,275.0 g |

The liquid extract contains 17.2% of HARPAGOPHYTON water-alcohol-soluble constituents. Its alcohol content is 30%. Its characteristic harpagoside constituent content is 1.2 g per 100 g of liquid extract.

Technical realisation

Mixture and granulation

All the cellulose is introduced into a mixer of the planetary type.

The mixer is turned at low speed (speed 1) and all the extractive plant solution is incorporated progressively and continuously. Agitation is effected for five minutes to homogenise the whole.

Extrusion

The moist mass is introduced into the axial twin-screw extruder provided with a die with an orifice of an average diameter of 800 microns and with a thickness of 800 microns.

The extrusion speed is 100 rev/min.

The extrusion period for a mass of 8,550 g of moist granulated microcrystalline cellulose is 15 minutes at a temperature lower than 30° C. (extrusion system temperature between 25° and 30° C.).

The extrudates are collected in a container.

Spheronisation

All the extrudates are introduced into a spheroniser 60 cm in diameter.

Spheronisation is effected in accordance with four cycles of variable speed and duration, controlled automatically by computer.

Cycle 1: 740 rev/min—180 seconds
Cycle 2: 740 rev/min—180 seconds
Cycle 3: 740 rev/min—180 seconds
Cycle 4: 500 rev/min—15 seconds The spheroids are collected in a container.

Drying

All the spheroids are introduced into a rotary turbine provided with a hot (40° C.) air supply device with ambient air induction.

The turbine is set in operation at low speed (speed 1) and the hot air is oriented tangentially to the bed of spheroids.

Operation is left to continue for one hour.

The residual moisture content is checked by weight. When this content is lower than 5% (m/m) of the mass, drying is stopped. If the reverse is true, the supply of hot air is maintained in ten minute stages until a residual moisture content lower than 5% (m/m) is reached.

Calibration

The dry spheroids are passed over an automatic calibrating device comprising two grids 1.000 mm and 0.350 mm in mesh diameter.

The spheroids between these two screens are packed in pockets of food quality polyethylene, sealed and labelled with the name of the galenic form, the name of the plant drug and the batch number.

Inspection

The granulometric yield of the calibrated spheroids is 97%. The water-alcohol-soluble constituent content is 17.0 g per 100 g of spheroids. The characteristic harpagoside constituent content is 1.15 g per 100 g of spheroids.

Example 2

A form of spheroids containing 11.7% of water-alcohol-soluble PASSIFLORA constituents corresponding to 100.0 parts of dried plant and having the following composition was prepared in the manner described above.

For a batch of approximately 5,600 g of spheroids the formula comprises:

| Ingredient | Quantity in % by weight |
| --- | --- |
| PASSIFLORA liquid extract | 5,100.0 g |
| Microcrystalline cellulose | 5,000.0 g |

The liquid extract contains 11.7% of water-alcohol-soluble PASSIFLORA constituents. Its alcohol content is 45%. Its heteroside content expressed as characteristic vitexine constituent is 0.85 g % grams of liquid extract.

The technical realisation of Example 1 was repeated.

Inspection

The granulometric yield of calibrated spheroids is 97%. The water-alcohol-soluble constituent content is 10.65 g per 100 g of spheroids. The heteroside content, expressed as characteristic vitexine constituent, is 0.77 g per 100 g of spheroids.

Example 3

A form of spheroids containing 4.7% of GINSENG water-alcohol-soluble constituents, 0.65% for ELEUTHERO- COCCUS corresponding to 100.0 parts of dried plants and of the following composition was prepared in the manner described above.

For a batch of approximately 5,650 g of spheroids the formula comprises:

| Ingredient | Quantity in % by weight |
| --- | --- |
| GINSENG liquid extract | 1,275.0 g |
| Extract of ELEUTHEROCOCCUS | 3,750.0 g |
| POLLEN | 27.5 g |
| Microcrystalline cellulose | 5,000.0 g |

Remarks

The liquid extract contains 4.7% of water-alcohol-soluble GINSENG constituents, 0.65 for ELEUTHEROCOCCUS. The alcohol contents are 25% in both cases.

Example 1 is repeated for the technical realisation after mixing the POLLEN with the microcrystalline cellulose.

Inspection

The granulometric yield of the calibrated spheroids is 96.5%. The water-alcohol-soluble constituent content is 1.65 g per 100 g of spheroids.

Example 4

A form of spheroids containing 2.4% of water-alcohol-soluble constituents of RED VINE corresponding to 100.0 parts of dried plant and having the following composition was prepared in the manner described above.

For a batch of approximately 5,100 g of spheroids the formula comprises:

| Ingredient | Quantity in % by weight |
| --- | --- |
| RED VINE liquid extract | 4,000.0 g |
| Lactose | 1,000.0 g |
| Microcrystalline cellulose | 4,000.0 g |

Remarks

The liquid extract contains 2.4% of water-alcohol-soluble RED VINE constituents. Its alcohol content is 45%. Its flavonoid content expressed as characteristic malvidin constituent is 0.3 g per 100 g of liquid extract.

Technical realisation

Inspection

The granulometric yield of calibrated spheroids is 95.6%. The water-alcohol-soluble constituent content is 1.88 g per 100 g of spheroids. The flavonoid content expressed as characteristic malvidin constituent is 0.23 g per 100 g of spheroids.

Example 5

A form of spheroids containing 0.0489% of zinc gluconate was prepared in the manner described above.

For a batch of approximately 5,000 g of spheroids the formula comprises:

zinc salt solution 5,400.0 g microcrystalline cellulose 5,000.0 g.

Example 6

A form of spheroids containing beta-carotenoid, provided by carrot juice, was prepared in the manner described above.

For a batch of approximately 5,000 g of spheroids the formula comprises:

carrot juice 5,200.0 g microcrystalline cellulose 5,000.0 g.

Example 7

A form of spheroids containing mineral elements provided by sea water was prepared in the manner described above.

For a batch of approximately 5,000 g of spheroids the formula comprises:

partially desalted sea water 5,200.0 g microcrystalline cellulose 5,000.0 g.

Remarks

The sea water may contain quantities of soluble components in the vicinity of 30 to 40%.

We claim:

1. A process for preparing orally absorbable spheroid containing an active ingredient from a plant material, said process comprising the steps of:

preparing a liquid extract containing an active ingredient from a plant material produced by dissolving said active ingredient in a solvent chosen from alcohol, water and mixture of alcohol and water;

selecting cellulose as a natural polymer;

moistening said cellulose with said liquid extract to form a moistened mass such that said cellulose adsorbs and absorbs substantially all of said active ingredient;

granulating said moistened mass by humidification;

extruding said moistened mass through an extrusion die having an orifice diameter and an orifice length dimension which have a relationship with one another of about 1 at an extrusion temperature below about 30 degrees celsius to form an extrudate;

spheronizing said extrudate to form spheroids via a rotary spheronizer with four phases which have a speed and a time duration of:

a first phase of about 740 revolutions per minute for 1.5 minutes;

a second phase of about 740 revolutions per minute for 1.5 minutes;

a third phase of about 740 revolutions per minute for minutes; and a fourth phase of about 500 revolutions per minute for seconds thereby forming said spheroids with a granulometry of between 350 and 1,000 microns and with a minimum yield of 95%; and drying said spheroids at a drying temperature below about 40 degrees celsius.

2. A process according to claim 1, further comprising the step of calibrating said spheroids by passing said spheroids over a screen comprising two superposed vibrating grids.

3. A process according to claim 1, further comprising the step of using microcrystalline cellulose as said cellulose and using a weight of said cellulose which is substantially equal to a weight of said liquid extract.

4. A process according to claim 1, further comprising the step of mixing an auxiliary substance with said cellulose.

5. A process according to claim 4, further comprising the step of using one of a low-energy sugar, an organic material and mineral material as said auxiliary substance.

6. A process according to claim 1, further comprising the step of homogenizing said moistened mass prior to granulating said moistened mass.

7. An orally absorbable spheroid containing an active ingredient from a plant material, .said spheroid produced by a process comprising the steps of:

preparing a liquid extract containing an active ingredient from a plant material produced by dissolving said active ingredient in a solvent chosen from alcohol, water and mixture of alcohol and water;

selecting cellulose as a natural polymer;

moistening said cellulose with said liquid extract to form a moistened mass such that said cellulose adsorbs and absorbs substantially all of said active ingredient;

granulating said moistened mass by humidification;

extruding said moistened mass through an extrusion die having an orifice diameter and an orifice length dimension which have a relationship with one another of about 1 at an extrusion temperature below about 30 degrees celsius to form an extrudate;

spheronizing said extrudate to form spheroids via a rotary spheronizer with four phases which have a speed and a time duration of:

a first phase of about 740 revolutions per minute for 1.5 minutes;

a second phase of about 740 revolutions per minute for 1.5 minutes;

a third phase of about 740 revolutions per minute for 1.5 minutes; and a fourth phase of about 500 revolutions per minute for 15 seconds thereby forming said spheroids with a granulometry of between 350 and 1,000 microns and with a minimum yield of 95%; and drying said spheroids at a drying temperature below and about 40 degrees celsius.

8. The spheroid according to claim 7, wherein the quantity of said liquid extract is between 50% and 250% by weight of said cellulose used for preparation of said spheroid.

9. The spheroid according to claim 7, wherein said liquid extract contains up to 30% of at least one alcohol soluble plant constituent.

10. The spheroid according to claim 7, wherein said liquid extract contains up to 30% of at least one of:

at least one plant constituent soluble in water; and at least one plant constituent soluble in a mixture of alcohol and water.

11. The spheroid according to claim 7, wherein at least one auxiliary substance is mixed with said cellulose.

12. The spheroid according to claim 11, wherein said at least one auxiliary substance is one of an organic substance and a mineral material.

13. The spheroid according to claim 11, wherein said at least one auxiliary substance is, selected from the group consisting of a simple sugar and a low-energy sugar.

14. The spheroid according to claim 11, wherein said at least one auxiliary substance is selected from the group consisting of lactose, sorbitol, D-mannitol, maltodextrins, ethylated cellulose derivatives methylated cellulose derivatives, carboxylated cellulose derivatives, gelatins, polyvinyl pyrrolidone, carbonates and citrates.

15. The spheroid according to claim 11, wherein said at least one auxiliary substance contains a microcrystalline cellulose constituting 20% to 80% of a total mass of said cellulose to be moistened, lactose constituting 20% to 80% of the total mass of said cellulose to be moistened, and one of gelatin of variable jellifying power or polyvinyl pyrrolidone or a cellulose derivative constituting less than 10% of the total mass of said cellulose to be moistened.

16. The spheroid according to claim 7, wherein said liquid extract containing said active ingredient from a plant material, for moistening the mass to be extruded, is used in a ratio of about 15% to 90% of the mass to be moistened.

17. The spheroid according to claim 7, wherein said spheroid is coated, or in the form of hard gelatin capsules or tablets for oral administration.

* * * * *